United States Patent [19]

Rogers

[11] 4,247,957
[45] Feb. 3, 1981

[54] ADJUSTABLE SUN VISOR

[75] Inventor: Sandra K. Rogers, Berwyn, Ill.

[73] Assignee: Champion International Corporation, Stamford, Conn.

[21] Appl. No.: 47,497

[22] Filed: Jun. 11, 1979

[51] Int. Cl.³ .......................... A42B 1/18; A42B 1/22
[52] U.S. Cl. .............................................. 2/12; 2/197
[58] Field of Search ..................... 2/12, 197, 200, 174, 2/192

[56] References Cited

U.S. PATENT DOCUMENTS

| 2,629,869 | 3/1953 | Locken | 2/197 X |
| 2,679,047 | 5/1954 | Bozzi | 2/12 |
| 2,988,743 | 6/1961 | Wagenfeld | 2/12 |

Primary Examiner—Peter P. Nerbun
Attorney, Agent, or Firm—Evelyn M. Sommer

[57] ABSTRACT

A unitary, adjustable sun visor comprising a sunshade panel having an inner arcuate surface, at least two arms extending rearwardly from said panel, and adjustable clasping means integrally formed with the outer portions of said arms.

4 Claims, 3 Drawing Figures

ADJUSTABLE SUN VISOR

BACKGROUND OF THE INVENTION

This invention relates to sun visors and in particular to sun visors made of a semi-rigid material such as paper board which can be economically formed from a unitary blank of paper board and yet be adjustable to different sizes so that any particular sun visor may be used by any particular individual by simply adjusting the size of a headband to fit the particular user. Further, such sun visors may be constructed in an economical manner from a semi-rigid material such as paper board wherein the visor portion may also be used to place advertising thereon and yet be a disposable item because of the economy by which they are constructed.

Prior art sun visors include those types which have a visor or sunshade portion to which is attached to headband made of an elastic material which thereby is adjustable to fit any particular user. However, such sun visors are expensive and difficult to make inasmuch as the elastic or stretchable headband must be attached in some manner to the rigid or semi-rigid visor or sunshade. Such visors, of course, are not of the disposable type because of their cost.

Other economical sunshades can be made of a semi-rigid material such as paper board but are of rigid or fixed size, thus necessitating each individual to use a particular visor of the proper size for him. The problem therefore is to construct a sun visor that is not only economical and simple to construct to that it can be a throw-a-way or disposable item but also to so construct it that it is of adjustable size whereby any one sun visor can be adjusted to the proper size for a particular individual.

SUMMARY OF THE INVENTION

Thus, the present invention is directed to a new and novel sun visor of unitary construction and formed from a single blank which not only can have advertising printed thereon and is disposable because of its economical cost but is also adjustable to various head sizes.

Thus, the invention relates to a unitary, adjustable sun visor comprising a sunshade panel having an inner arcuate surface, at least two arms extending rearwardly from said panel, and adjustable clasping means integrally formed with the outer portions of said arms.

Briefly stated, the invention comprises a unitary, adjustable size sun visor of semi-rigid material comprising a sunshade panel having an inner arcuate surface formed by rearwardly extending arms and adapted to generally fit the forehead of the wearer and an adjustable headband comprising first and second arcuate strips integrally formed with and extending rearwardly from the respective outer ends of said arms, each of said strips having at least one slot therein whereby each strip may be inserted in the slot in the other strip thereby forming a sun visor of variable size.

The invention also comprises a blank of semi-rigid material for forming an adjustable sun visor comprising a visor portion having an inner arcuate surface adapted to generally fit the forehead of the wearer, an arcuate headband integrally formed with, extending rearwardly from and connecting the respective outer ends of said arcuate surface of said visor, perforations in said headband for detachably separating said headband into first and second parts and perforations extending partially across both said first and second parts whereby when said headband is separated into said first and second parts, said perforations may be torn to form slots to be inserted in each other thereby detachably connecting said first and second parts to form an adjustable size headband.

BRIEF DESCRIPTION OF THE DRAWINGS

These and other objects and advantages of the present invention will be disclosed in the course of the following specifications, reference being had to the accompanying drawings in which.

DETAILED DESCRIPTION OF THE DRAWINGS

Figure 1:
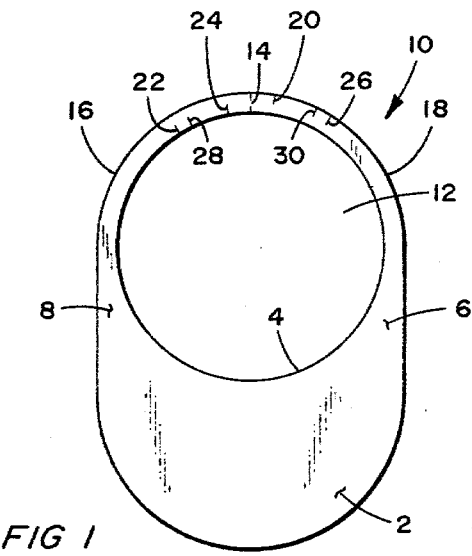
FIG. 1 is a plan view of the preferred embodiment of the novel, unitarily constructed, adjustable size sun visor.

FIG. 1 is a plan view of the preferred embodiment of the novel adjustable sun visor and is formed by stamping or otherwise cutting the design shown in FIG. 1 from a piece of paper board such as for example, 0.016 inch thick SBS type. As can be seen in the plan view of FIG. 1, the novel sun visor is of one piece construction including a panel, visor or sunshade 2 which has an inner arcuate portion 4 curved to fit the forehead of the user and shaped to shield the eyes of the user from the sun. Inner arcuate surface 4 is formed by rearwardly extending arms 6 and 8. Headband 10 is arcuate in shape, integrally formed with, extends rearwardly from and connects respective outer ends of arms 6 and 8. The circular orifice 12 thus formed in the visor may be of any particular diameter such as, for example only, having a diameter of approximately 8 inches. This diameter of course determines the largest size of the visor. Headband 10 has perforations 14 therein which may be broken or torn apart to separate headband 10 into first and second parts 16 and 18 respectively. Slots, or perforations which may be torn to form slots, are formed in each of said first and second parts to allow headband 10 to be adjusted to various sizes. Thus, once first and second parts 16 and 18 of headband 10 have been torn into two separate parts by tearing perforations 14, slot 20 in part 18 may be inserted in slot 22 of part 16 and slot 24 of part 16 may be inserted in slot 26 of part 18 to form the smallest size sun visor. If a slightly larger size is needed, slot 20 in part 18 may be inserted in slot 28 of part 16 while slot 24 of part 16 may be inserted in slot 30 of part 18. If still a larger size sun visor is needed, slot 20 in part 18 may be inserted in slot 24 of part 16. Thus, it can be seen that by providing a plurality of slots in headband parts 16 and 18, various headband sizes may be formed simply by choosing the proper combination of slots in one arm to be inserted in the desired slot in the other part.

It will be noted that in headband part 16, slots 22, 24 and 28 extend partially across the headband strip 16 from the inside while slots 20, 26 and 30 in headband part or strip 18 extend partially across strip 18 from the outside. This construction allows easy insertion of the slots of one part of the headband into the slots of the other part of the headband to vary the size thereof. However, the slots in both parts or strips 16 and 18 of the headband could extend partially across strips 16 and 18 from either the outside or the inside and still allow an interlocking action of the two headband parts 16 and 18 when the slots are inserted in each other. Obviously, as many slots may be placed in parts 16 and 18 of the headband as desired to form a multiplicity of visor sizes. Further, while slots can be used as stated earlier, it is preferable that perforations be used which can be torn to form the slots because the headband has more stability and resists tearing when only those perforations are torn that are necessary to form the slots required for a particular size. The other perforations remaining intact form a solid headband which is less likely to tear with use. Thus, the perforations are preferable over actual slots.

Visor or sunshade portion 2 can have advertising printed thereon or other printing matter as desired.

Thus, the unique features of this sun visor are the adjustment of the headband part for various sizes while the structure requires no additional pieces or any gluing in the production process. The perforations or slots on the headband parts correspond to various head sizes such as small, medium and large. When the first and second parts 16 and 18 of the headband are locked into place, the visor 2 is caused to curve as in a typical visor.

Figure 2:
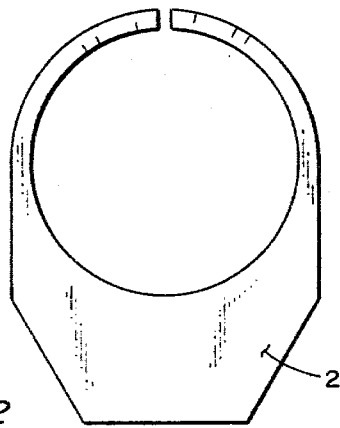
FIG. 2 is an alternate embodiment of the novel sun visor having a visor portion or sunshade portion of different construction than the embodiment illustrated in FIG. 1.

FIG. 2 illustrates an alternate embodiment of the novel sun visor having a different shaped visor or sunshade 2. Obviously any desired shape could be used for the sunshade or visor 2.

Figure 3:
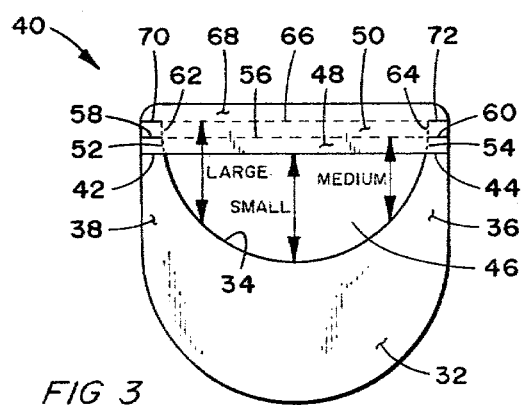
FIG. 3 is a plan view of a second alternate embodiment of the novel adjustable sun visor illustrating a different construction for enabling the sun visor to have an adjustable size.

A second alternate embodiment of the novel sun visor is illustrated in plan view in FIG. 3. Again, the visor is formed of unitary construction and is made preferably of paper board such as the type designated 0.016 SBS.

The sunshade or visor portion 32 in its preferred form is the arcuate shape as illustrated in FIG. 3 but of course could also be of a shape such as that shown in FIG. 2 or any other desired shape. Again, visor portion 32 has an inner arcuate surface 34 formed by rearwardly extending arms 36 and 38. Arms 36 and 38 are integrally formed with visor portion 32. A generally rectangular shaped panel 40 is also integrally formed with and hingedly connected with the respective ends of arms 36 and 38 by means of score lines 42 and 44 thereby forming a semi-circular head opening 46 with said arcuate surface 34. Thus, the smallest size of the visor is that illustrated in FIG. 3 wherein rectangular panel 40 forms the semi-circular opening 46 with arcuate surface 34.

However, rectangular panel 40 has a plurality of abutting, detachable strips such as strips 48 and 50 integrally formed in consecutive order on the side of said rectangular panel 40 facing inwardly toward said semi-circular head opening 46 whereby each strip 48 and 50 may be removed as necessary in consecutive order thereby increasing the size of the semi-circular head opening 46.

Thus, detachable strip 48 is integrally formed with and detachably connected to rectangular panel 40 by end perforations 52 and 54 and side perforations 56. To make a larger size sun visor, strip 48 may be partially torn along the end perforations 52 and 54 and, since the paper board is only semi-rigid, it will flex at the point where the tear in the perforations 52 and 54 stop thus allowing a larger head space to be formed by semi-circular opening 46. If desired, the entire strip 48 can be removed by tearing perforations 52, 54 and 56. The remaining portion of rectangular panel 40 can then be flexed at score lines 58 and 60 which are aligned with base line 56 of strip 48 to fold up or down against the back of the head and form a substantially flat headband. If still a larger size is required, detachable strip 50 can be either entirely or partially removed in the same manner as described for strip 48 thus increasing further the semi-circular head space portion 46. If detachable strip 50 has only a partial breakage of perforations 62 and 64 on the ends thereof, another intermediate size can be obtained. If the entire strip is removed by tearing the perforations 62, 64 and 66, the remaining strip 68 can bend about score lines 70 and 72 to form a substantially flat headband against the back of the head and thus allow the largest semi-circular head opening 46.

This design minimizes paper waste by utilizing score lines and bending of the paper board. Three sizes are thus achieved by the example illustrated in FIG. 3 although of course more than two detachable strips 48 and 50 could be utilized if desired. The successive scores and perforations allow the three sizes to be achieved as illustrated in FIG. 3. For the smallest size, the visor would remain as illustrated in FIG. 3. The second size is obtained by breaking or tearing perforated lines 52, 54 and 56 and tearing out panel 48. The remainder of rectangular panel 40 is then folded about score lines 58 and 60 which are aligned with the base line 56 of strip 48. The largest size is achieved in the same way by tearing out detachable strip 50 along score lines 62, 64 and 66 and folding the remaining strip 68 of rectangular panel 40 about score lines 70 and 72 which are aligned with the base line 66 of strip 50. Intermediate sizes may be obtained by partially breaking the end perforations 52 and 54 of strip 48, or perforations 62 and 64 of detachable strip 50 if strip 48 is removed. This would leave the detachable strips partially attached to the structure thus creating pressure against the head for a "custom" fit. It will be noted that perforations 52 and 54 and 62 and 64 on the ends of strips 48 and 50 respectively slope generally outwardly in an arcuate manner thereby continually maintaining a generally semi-circular head opening as each strip 48 and 50 is removed.

Again, for construction purposes the waste of paper is minimal as a result of the flat unitary construction. Edges of the visors are adjacent to each other when punched or otherwise cut from paper stock. Again, no additional pieces are required, there is no gluing in production and the shape is dictated according to individual customer needs.

While the invention has been described in connection with a preferred embodiment and two alternate embodiments, it is not intended to limit the scope of the invention to the particular forms set forth but on the contrary, it is intended to cover such alternatives, modifications and equivalents as may be included within the spirit and scope of the invention as defined by the appended claims.

What is claimed is:

1. A unitary adjustable sun visor of semi-rigid material comprising:
   a visor portion having an inner arcuate edge defined by rearwardly extending arms and adapted to fit generally over the forehead of the wearer; and
   a longitudinally extending, generally rectangular panel having opposed long and short sides, said rectangular panel being integrally formed with said visor portion and connected to the extending arms thereof along one of said long sides of said panel thereby defining a semi-circular head opening with said arcuate edge, said rectangular panel including a pair of spaced perforations starting on said one long side of said rectangular panel and extending to a point intermediate the width of said panel, said perforations being arcuate in configuration, and essentially a continuation of said arcuate edge, whereby when said visor is to be worn, a portion of said rectangular panel is folded along a line parallel to the longitudinal axis of said panel thereby forming a substantially flat headband surface and wherein the size of said head opening may be varied by tearing said perforations and folding said rectangular panel along a line coincident with the end points of the tears of said perforations, such that a larger opening is formed.

2. A sun visor as in claim 1 wherein said semi-rigid material is 0.016 inch thick paper board.

3. A sun visor as recited in claim 1 wherein said rectangular panel further includes a plurality of perforated lines extending between said pair of perforations and parallel to the longitudinal axis of said panel and defining detachable rectangular strips, said strips being removable to facilitate the adjustment of the size of said head opening.

4. A sun visor as recited in claim 3 further including a plurality of fold lines formed in said rectangular panel starting from the short sides thereof, and extending to the associated spaced perforation, said fold lines being colinear with the perforated lines defining said detachable rectangular strips, said fold lines to facilitate the folding of said rectangular panel.

* * * * *